United States Patent
Higgins et al.

(10) Patent No.: US 10,764,667 B2
(45) Date of Patent: Sep. 1, 2020

(54) EAR-WEARABLE DEVICE HAVING TUNNEL WITH ELECTRICAL CONTACT PINS

(71) Applicant: Starkey Laboratories, Inc., Eden Prairie, MN (US)

(72) Inventors: Sidney A. Higgins, Maple Grove, MN (US); David Tourtelotte, Eden Prairie, MN (US); Mohammed Alshehri, St. Louis Park, MN (US); Mark Farley, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 16/213,719

(22) Filed: Dec. 7, 2018

(65) Prior Publication Data
US 2020/0186903 A1 Jun. 11, 2020

(51) Int. Cl.
*H04R 1/10* (2006.01)
*A61B 5/00* (2006.01)
*H04R 25/00* (2006.01)

(52) U.S. Cl.
CPC .......... *H04R 1/1016* (2013.01); *A61B 5/6817* (2013.01); *H04R 25/60* (2013.01); *H04R 25/65* (2013.01); *H04R 2225/025* (2013.01)

(58) Field of Classification Search
CPC ...... H04R 25/65; H04R 25/60; H04R 1/1016; H04R 2225/025; A61B 85/6817
See application file for complete search history.

(56) References Cited

U.S. PATENT DOCUMENTS

| | | | |
|---|---|---|---|
| 8,953,827 B2 | 2/2015 | Sacha et al. | |
| 9,819,075 B2 | 11/2017 | Kerselaers et al. | |
| 10,390,154 B2 | 8/2019 | Spearman et al. | |
| 2004/0107080 A1 | 6/2004 | Deichmann et al. | |
| 2005/0244024 A1 | 11/2005 | Fischer et al. | |
| 2008/0164770 A1* | 7/2008 | Terlizzi | B21C 23/18 307/125 |
| 2008/0304686 A1 | 12/2008 | Meskens et al. | |

FOREIGN PATENT DOCUMENTS

| | | | | |
|---|---|---|---|---|
| DE | 102008024515 B3 * | 4/2010 | ............. | H04R 25/55 |
| DE | 102008024515 B3 | 4/2010 | | |
| KR | 20040107056 A | 12/2004 | | |

OTHER PUBLICATIONS

U.S. Appl. No. 16/213,672, filed Dec. 7, 2018, by Stewart et al.
International Search Report and Written Opinion from International Application No. PCT/US2019/064733, dated Feb. 13, 2020, 19 pp.

* cited by examiner

*Primary Examiner* — Sunita Joshi
(74) *Attorney, Agent, or Firm* — Shumaker & Sieffert, P.A.

(57) ABSTRACT

An ear-wearable device includes a shell shaped for wearing in a user's ear. The shell comprises a tunnel wall shaped to define a tunnel that passes through the ear-wearable device. The tunnel wall defines one or more contact pin apertures through which distal ends of two or more contact pins pass. One or more electrical components are encased within the shell. The contact pins are conductors from the one or more electrical components. The distal ends of the contact pins are positioned to make electrical contact with terminals of a cable plug that is removably inserted into the tunnel.

17 Claims, 8 Drawing Sheets

EAR-WEARABLE DEVICE HAVING TUNNEL WITH ELECTRICAL CONTACT PINS

TECHNICAL FIELD

This disclosure relates to ear-wearable devices.

BACKGROUND

An ear-wearable device is a device designed to be worn on or in a user's ear. Example types of ear-wearable devices include hearing aids, earphones, earbuds, telephone earpieces, and other types of devices designed to be worn on or in a user's ear.

In-ear wearable devices are ear-wearable devices designed to be worn at least partially in the user's ear canal. For example, Invisible-In-The-Canal (IIC) hearing aids, Completely-In-Canal (CIC) hearing aids, In-The-Canal (ITC) hearing aids, In-The-Ear (ITE) hearing aids, and the receiver portions of Receiver-In-Canal (MC) hearing aids are designed to be worn in the user's ear canals. One advantage of in-ear wearable devices over other types of ear-wearable devices is that in-ear wearable devices may be less visible than other types of ear-wearable devices.

Because an in-ear wearable device is worn in a user's ear canal, the in-ear wearable device may need to have a vent that allows sound generated within the user's head (e.g., the user's voice, chewing sounds, etc.) to escape the user's ear canal instead of being trapped and resonating within the user's ear canal. The user may experience discomfort when such internally generated sounds resonate in the user's ear canal.

SUMMARY

This disclosure describes an ear-wearable device having a shell shaped to define a tunnel, such as a vent, that passes through the ear-wearable device. Contact pins are situated in the tunnel and may be immovable relative to the shell. A cable plug of a cable may be inserted into the tunnel such that terminals located on the cable plug come into electrical contact with the contact pins. The contact pins may form conductors to one or more electrical components situated in the ear-wearable device.

In one example, this disclosure describes an ear-wearable device comprising: a shell shaped for wearing in an ear of a user, wherein the shell comprises a tunnel wall, the tunnel wall being a portion of the shell shaped to define a tunnel that is open-ended and passes through the ear-wearable device; two or more contact pins positioned within the shell; the tunnel wall being shaped such that the tunnel wall defines one or more contact pin apertures through which distal ends of the contact pins pass; one or more electrical components encased within the shell, the contact pins being conductors from the one or more electrical components; and wherein the distal ends of the contact pins are positioned to make electrical contact with terminals of a cable plug that is removably inserted into the tunnel.

In another example, this disclosure describes a system comprising: a cable having a cable plug; and an ear-wearable device comprising: a shell shaped for wearing in an ear of a user, wherein the shell comprises a tunnel wall, the tunnel wall being a portion of the shell shaped to define a tunnel that is open-ended and passes through the ear-wearable device; two or more contact pins positioned within the shell; the tunnel wall being shaped such that the tunnel wall defines one or more contact pin apertures through which distal ends of the contact pins pass; one or more electrical components encased within the shell, the contact pins being conductors from the one or more electrical components; and wherein the distal ends of the contact pins are positioned to make electrical contact with terminals of the cable plug that is removably inserted into the tunnel.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

An ear-wearable device may contain a rechargeable battery that provides electrical energy to various electronic components of the in-ear wearable device. Additionally, it may be desirable for in-ear wearable devices to have cable-based communication capabilities. However, attaching power and communication cables to in-ear wearable devices has proven to be challenging. Many ear-wearable devices are tailored to fit the unique anatomical shapes of individual users' ear canals. The resulting variability in the size and shape of in-ear wearable devices may make it difficult to design places to attach cables to the in-ear wearable devices. Additionally, in prior ear-wearable devices, attachment points of such cables may involve moving parts that are susceptible to debris or water intrusion and may be prone to mechanical fatigue.

As noted above, many ear-wearable devices may have vents that allow internally-generated sound to exit the user's ear canal from portions of users' ear canals medial to the ear-wearable devices and the outside environment. Thus, an ear-wearable device may have a shell molded for wear in an ear of a user. For instance, the shell may be shaped such that at least a portion of the shell may be inserted into an ear canal of an ear of the user. The shell has a lateral surface and a medial surface. The lateral surface of the shell is distal to a midline of the user when the ear-wearable device is worn by the user. The medial surface of the shell is proximal to the midline of the user when the ear-wearable device is worn by the user. Furthermore, the shell has a tunnel wall. The tunnel wall is a portion of the shell shaped to define a tunnel that passes through the in-ear wearable device from the lateral surface of the shell to the medial surface of the shell and is open at both the lateral surface of the shell and the medial surface of the shell.

In accordance with the techniques of this disclosure, two or more contact pins are positioned within the shell. The contact pins are conductors from one or more electrical components (e.g., a battery, processor, etc.) that are encased within the shell. The tunnel wall defines one or more contact pin apertures through which distal ends of the contact pins pass. For example, the tunnel wall may define a first contact pin aperture through which a distal end of a first contact pin passes and the tunnel wall may define a second contact pin aperture through which a distal end of a second contact pin passes. In another example, the tunnel wall may define a contact pin aperture through which the distal ends of both a first contact pin and a second contact pin pass. The distal ends of the contact pins are positioned to make electrical contact with terminals of a cable plug that is removably inserted into the tunnel.

Furthermore, in some examples, an elastomeric spring pad may be disposed on the shell of the ear-wearable device. Pressure applied by the elastomeric spring pad to the cable plug when the cable plug is inserted into the tunnel forces the terminals of the cable plug into electrical contact with the distal ends of the contact pins. For instance, the pressure applied by the elastomeric spring pad may force a first terminal of the cable plug into electrical contact with the distal end of a first contact pin and may force a second terminal of the cable plug into electrical contact with the distal end of a second contact pin. The cable plug may be the tip of a charging and/or communication cable.

Because the contact pins are in the tunnel, it may be unnecessary for there to be a separate opening in the ear-wearable device to insert the cable plug. This may save space within the ear-wearable device, e.g., for other components or may reduce the overall size of the ear-wearable device. Moreover, this may allow for more optimal placement of other components, such as antennas, telecoils, push buttons, rotary volume controls, and so on. Furthermore, because the contact pins are in the tunnel, they are not exposed on the outer surface of the ear-wearable device where they may more easily damaged.

Moreover, in prior ear-wearable devices that include a separate socket into which the tip of a cable in inserted, debris can accumulate in the socket. This debris may prevent the terminals of a cable plug from making good contact with contact pins in the socket. The debris may be difficult to remove without special tools. However, in the examples of this disclosure, because the contact pins are in the tunnel and the tunnel is open at both the lateral and medial surfaces of the ear-wearable devices, any debris that falls into the tunnel can simply be pushed out one side of the tunnel by inserting any small thin object into the other side of the tunnel.

Furthermore, prior ear-wearable devices have used moving contact pins, such as spring-loaded pogo pins and contact arms, to provide electrical connections to the terminals of cable plugs. However, moving contact pins are prone to failure due to debris ingress and/or mechanical fatigue failures. Ear-wearable devices manufactured in accordance with the techniques of this disclosure do not include moving contact pins. The elastomeric spring pad may provide enough force to ensure that the terminals of the cable plug are in electrical contact with the contact pins in the tunnel of the ear-wearable device.

Figure 1:
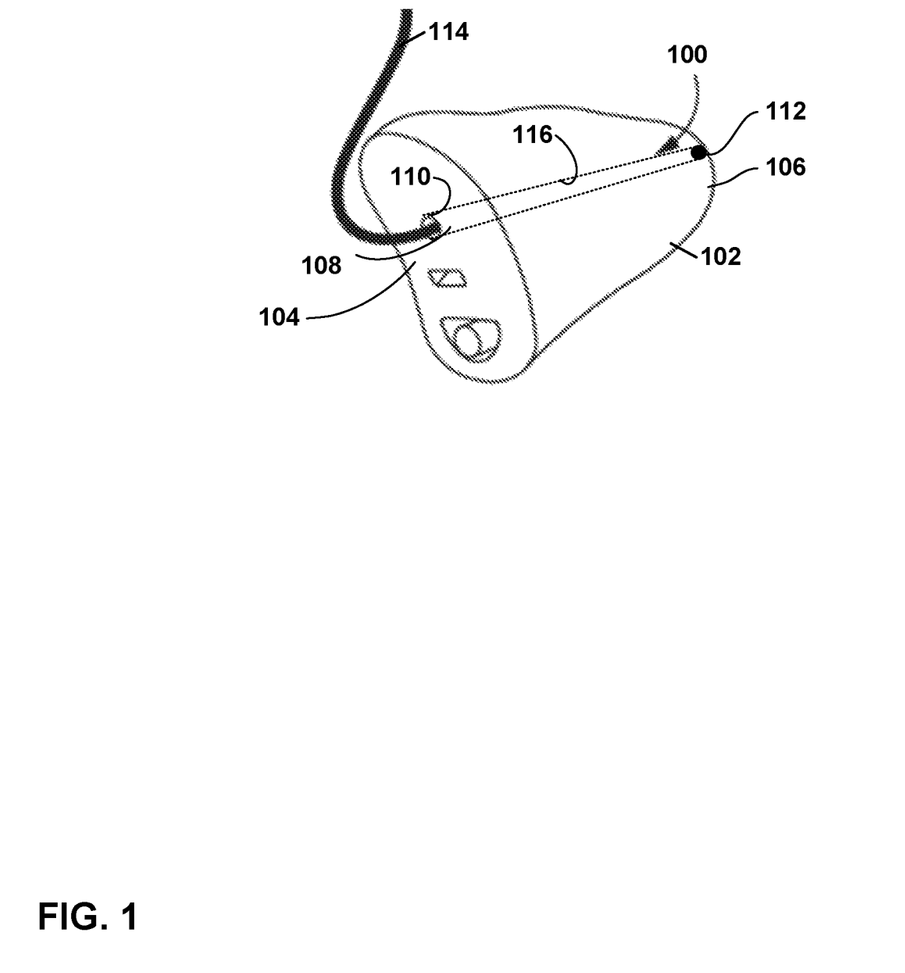
FIG. 1 illustrates an example ear-wearable device in accordance with one or more techniques of this disclosure.

FIG. 1 illustrates an example ear-wearable device 100. Ear-wearable device 100 may be a hearing aid, earphone, earbud, telephone earpiece, and another type of device designed to be worn on or in a user's ear. As shown in FIG. 1, ear-wearable device 100 includes a shell 102. Shell 102 is molded into a shape that can be worn in an ear of a user. For instance, shell 102 may be molded into a shape suitable for insertion into an ear canal of a user. In some examples, ear-wearable device 100 may be an in-the-ear device and shell 102 may be molded for wear outside an ear canal of a user. In some examples, shell 102 may be custom molded to fit the unique anatomy of an individual user's ear and/or ear canal. In some examples, shell 102 may be made of a flexible material or an elastomer, such as silicone rubber or other flexible material. Shell 102 may have different shapes and styles than that shown in the example of FIG. 1.

Shell 102 has a lateral surface 104 and a medial surface 106. In some examples, lateral surface 104 is a faceplate of ear-wearable device 100. Lateral surface 104 of shell 102 is distal to a midline of the user when ear-wearable device 100 is worn by the user. The midline of the user is considered to be a plane running vertically through the center of the user's body when the user is standing, the plane running from the anterior side of the user's body to the posterior side of the user's body. Medial surface 106 of shell 102 is proximal to the midline of the user when ear-wearable device 100 is worn by the user.

Shell 102 includes a tunnel wall 116. Tunnel wall 116 is a portion of shell 102 shaped to define a tunnel 108 that passes through ear-wearable device 100 from lateral surface 104 to medial surface 106. Tunnel 108 is open at both ends. Thus, tunnel wall 116 defines tunnel 108 such that tunnel 108 has a lateral portal 110 and a medial portal 112. In some examples, tunnel 108 may be a vent that allows internally-generated source to escape from a portion of the user's ear canal medial to ear-wearable device 100 and the outside environment. Thus, in some such examples, shell 102 may be shaped such that during wear of ear-wearable device 100, medial portal 112 of tunnel 108 is located inside an ear canal of the ear of the user. In some examples, shell 102 is shaped such that during wear of ear-wearable device 100, medial portal 112 of tunnel 108 is located in a concha of the ear of the user. Because tunnel 108 is open at both ends, debris may be cleaned from tunnel 108 by pushing the debris out an opposite end of tunnel 108.

As shown in the example of FIG. 1, a tip of cable 114 may be inserted into lateral portal 110 of tunnel 108. As described in greater detail elsewhere in this disclosure, contact pins positioned within tunnel 108 may come into electrical contact with terminals at a tip of cable 114 (i.e., a cable plug) when the tip of cable 114 is inserted into lateral portal 110 of tunnel 108. This may enable a user to use cable 114 to recharge a battery of ear-wearable device 100, exchange data between ear-wearable device 100 and another device, or perform other activities. In some examples, the contact pins positioned within tunnel 108 may come into electrical contact with the terminals at the tip of cable 114 when the tip of cable 114 is inserted into medial portal 112 of tunnel 108.

To summarize, ear-wearable device 100 comprises a shell 102 shaped for wearing in an ear of a user. Shell 102 comprises tunnel wall 116. Tunnel wall 116 is a portion of the shell shaped to define a tunnel that is open-ended and passes through ear-wearable device 100. Two or more contact pins are positioned within shell 102. Tunnel wall 116 is shaped such that tunnel wall 116 defines one or more contact pin apertures through which distal ends of the contact pins pass. One or more electrical components (e.g., batteries, processors, etc.) are encased within shell 102. The contact pins are conductor from the one or more electrical components. The distal ends of the contact pins are positioned to make electrical contact with terminals of a cable plug that is removably inserted into tunnel 108. For example, when the cable plug is inserted into tunnel 108, a first terminal of the cable plug is in electrical contact with the distal end of the first contact pin and a second terminal of the cable plug is in electrical contact with the distal end of the second contact pin.

Lateral portal 110 of tunnel 108 may have various shapes. For example, lateral portal 110 may be circular in shape. Thus, in this example, if the cable plug is also round, the cable plug may be able to rotate in tunnel 108 to a position desired by a user. In other examples, at least a portion of the cable plug that engages lateral portal 110 is oval, square, rectangular, or another non-circular shape that prevents the cable plug from rotating in tunnel 108.

Figure 2:
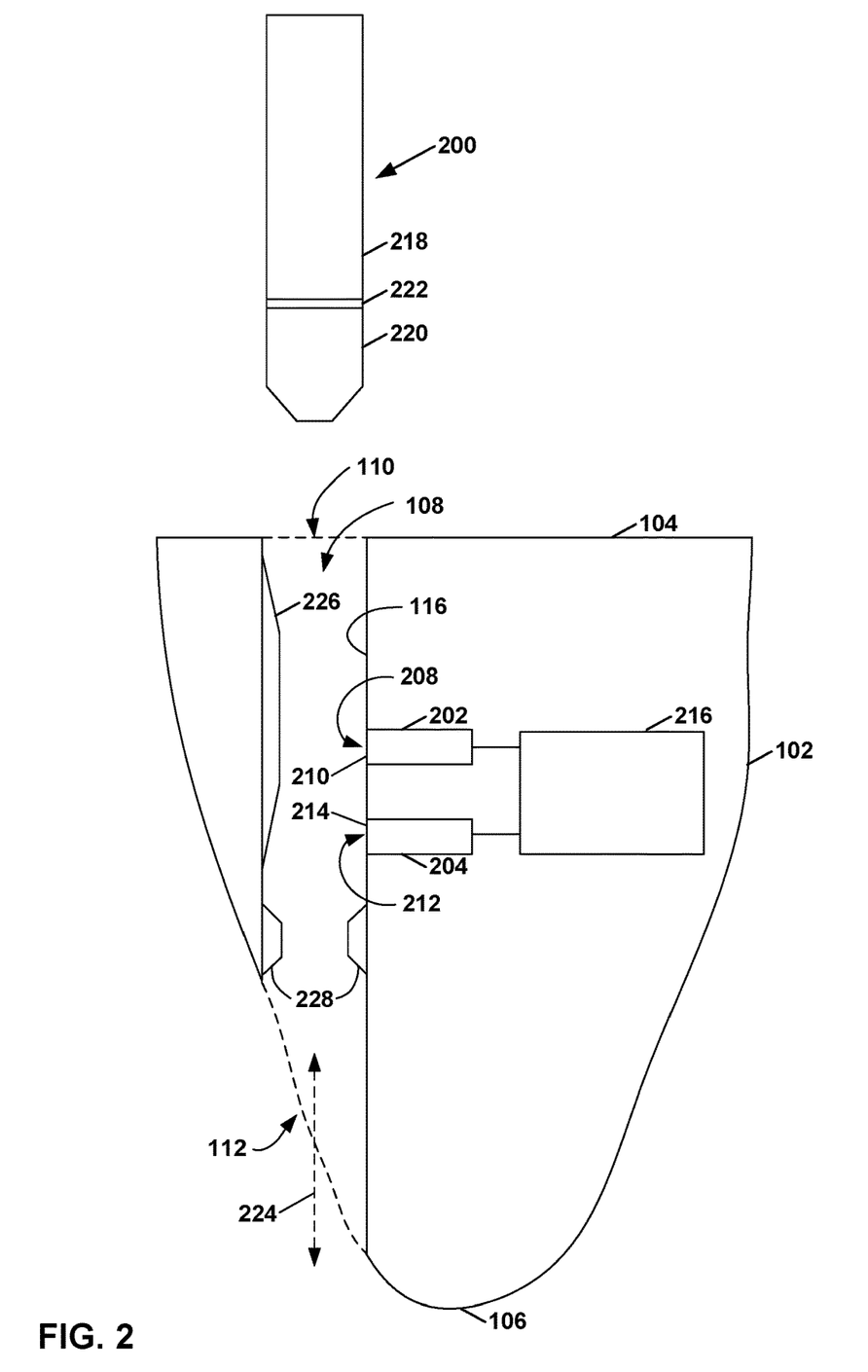
FIG. 2 is a conceptual diagram illustrating an example cross-section of ear-wearable device and a cable plug of a cable.

FIG. 2 is a conceptual diagram illustrating an example cross-section of ear-wearable device 100 of FIG. 1 and a cable plug 200 of cable 114 of FIG. 1. As shown in FIG. 2, a first contact pin 202 and a second contact pin 204 are positioned within shell 102. In other examples, additional contact pins may be positioned within shell 102. Shell 102 includes a tunnel wall 116 that is shaped to define tunnel 108. Furthermore, in the example of FIG. 2, tunnel wall 116 defines a contact pin aperture 208 through which a distal end 210 of contact pin 202 passes. In the example of FIG. 2, tunnel wall 116 also defines a second contact pin aperture 212 through which a distal end 214 of contact pin 204 passes. Tunnel wall 116 may be considered to be limited to the tube-shaped portion of shell 102 from lateral portal 110 of tunnel 108 through ear-wearable device 100 to medial portal 112 of tunnel 108.

In some examples, contact pin 202 and contact pin 204 are mounted within shell 102 such that contact pin 202 and contact pin 204 are immovable relative to shell 102. For instance, in the example of FIG. 2, contact pin 202 and contact pin 204 are not designed for movement in a direction parallel or orthogonal to lengthwise axis 224 of tunnel 108. Because contact pin 202 and contact pin 204 are immovable relative to shell 102, contact pin 202 and contact pin 204 are not moving parts and may therefore be less susceptible to debris intrusion or mechanical fatigue than moving parts like pogo pins. Furthermore, because contact pin 202 and contact pin 204 are immovable relative to shell 102, shell 102 can be made waterproof or water-resistant. Thus, in some such examples, ear-wearable device 100 may be submersible, even allowing the user to wear ear-wearable device 100 while swimming or showering.

One or more electrical components 216 are encased within shell 102. Contact pin 202 is a first conductor from electrical components 216. Distal end 210 of contact pin 202 may be a first terminal of the first conductor. Contact pin 204 is a second conductor from electrical components 216. Distal end 214 of contact pin 204 may be a second terminal of the second conductor. For instance, distal end 210 of contact pin 202 may be a positive terminal and distal end 214 of contact pin 204 may be a negative terminal.

Electrical components 216 may comprise various types of electrical or electronic components. For example, electrical components 216 may include a rechargeable battery. In other words, ear-wearable device 100 may comprise a battery configured to be recharged using electrical energy supplied through cable plug 200, contact pin 202, and contact pin 204. In such examples, the configuration of contact pins 202, 204 may support standard and high-speed charging. In some examples, electrical components 216 include communication units configured to receive information from other computing devices. For instance, in one example, a communication unit may be configured to receive data that configures ear-wearable device 100 for processing sound for a user. In other words, electrical components 216 may comprise circuitry configured to process data transmitted to ear-wearable device 100 through cable plug 200, contact pin 202, and contact pin 204. In some examples, a communication unit may be configured to receive media data.

In some examples, ear-wearable device 100 may include more than the two contact pins shown in FIG. 2. For instance, in one example, the one or more electrical components 216 may include a battery configured to be recharged using electrical energy supplied through the cable plug and a first set of two or more of the contact pins, and other ones of the electrical components 216 may be configured to process data transmitted to ear-wearable device 100 through cable plug 200 and a second set of two or more of the contact pins, which may include one or more contact pins different from the first set of contact pins.

As shown in the example of FIG. 2, cable plug 200 may be cylindrical in shape with a beveled tip. Cable plug 200 includes a first terminal 218 and a second terminal 220. Terminal 218 and terminal 220 may be separated by an insulator 222. In examples where cable plug 200 is cylindrical in shape, terminal 218, terminal 220, and insulator 222 may be in the form of concentric cylinders with terminal 220 being the innermost cylinder, insulator 222 being the middle cylinder, and terminal 218 being the outermost cylinder. In other words, insulator 222 may be positioned within cable plug 200 between terminals 218 and 220. Thus, terminal 218 and terminal 220 may extend 360-degrees around cable plug 200, thereby potentially allowing 360 rotation of cable plug 200 while terminal 218 and terminal 220 maintain electrical contact with contact pin 202 and contact pin 204. Terminal 218 may be connected to a first wire in the cable and terminal 220 may be connected to a second wire in cable 114 (FIG. 1). Thus, in the example of FIG. 2, cable plug 200 may have a similar configuration to headphone jacks commonly found in personal media players and smartphones. In examples where cable plug 200 includes additional terminals, the additional terminals may be concentrically nested in a similar manner.

In other examples, cable plug 200 may have other shapes. For example, cable plug 200 may be cuboid in shape. In this example, terminals of cable plug 200, such as terminal 218 and terminal 220, may be arranged next to each other along an axis orthogonal to or parallel to a lengthwise axis 224 of tunnel 108, or in other arrangements.

Furthermore, as shown in the example of FIG. 2, ear-wearable device 100 may include an elastomeric spring pad 226 disposed on shell 102. Pressure applied by elastomeric spring pad 226 to cable plug 200 when cable plug 200 is inserted into tunnel 108 may force terminal 218 of cable plug 200 into electrical contact with distal end 210 of contact pin 202 and may force terminal 220 of cable plug 200 into electrical contact with distal end 214 of contact pin 204. Additionally, pressure applied by elastomeric spring pad 226 may help to secure cable plug 200 into tunnel 108.

Figure 3:
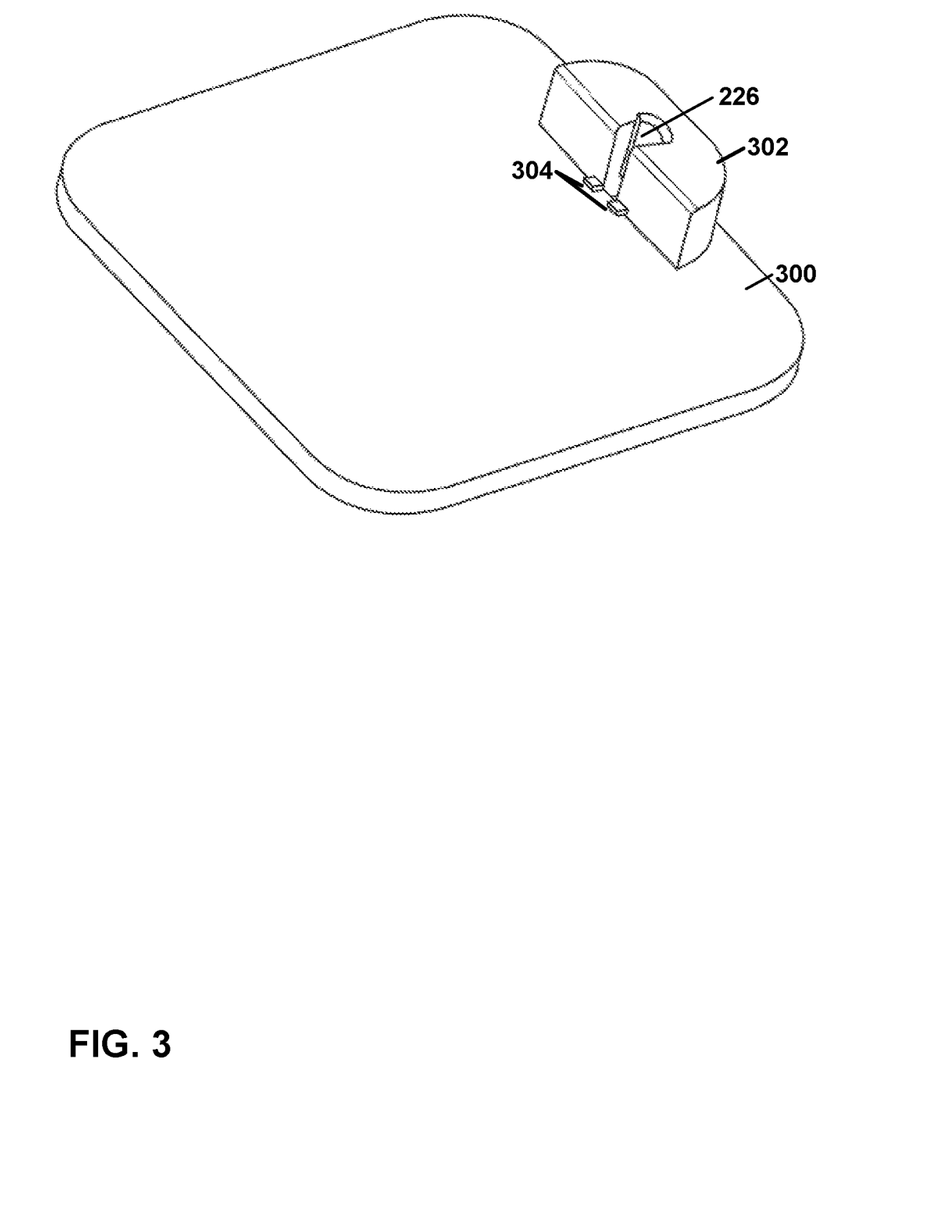
FIG. 3 is an illustration of an example faceplate manufactured in accordance with a technique of this disclosure.

Elastomeric spring pad 226 may be positioned at various locations on shell 102. For example, elastomeric spring pad 226 may be positioned on a portion of tunnel wall 116 opposite contact pin 202 and/or contact pin 204 as shown in FIG. 3. In another example, elastomeric spring pad 226 may be at a position on tunnel wall 116 separated by 90° from contact pin 202 and contact pin 204. In some examples, elastomeric spring pad 226 may be integral to shell 102 and/or tunnel wall 116. In other examples, elastomeric spring pad 226 be a separate piece that is bonded to or otherwise affixed to shell 102 and/or tunnel wall 116 at manufacturing time or another time. For example, elastomeric spring pad 226 may be bonded to tunnel wall 116 or 2-shot molded in place in tunnel wall 116.

Elastomeric spring pad 226 may be comprised of various types of materials that deform from their original shape when stress is applied and that reform to their original shapes when the stress is removed. Example types of materials suitable for use in elastomeric spring pad 226 may include silicone rubber or other elastomeric materials.

In some examples, ear-wearable device 100 does not include a distinct elastomeric spring pad. Rather, in some such examples, tunnel wall 116 itself, or a portion thereof, may comprise an elastomeric material such that when cable plug 200 is not in tunnel 108, a dimension (e.g., a diameter, width, height, etc.) of tunnel 108 is smaller than a corresponding dimension of cable plug 200 and when cable plug 200 is in tunnel 108, the dimension of tunnel 108 is expanded to the dimension of cable plug 200.

Although not shown in the example of FIG. 2, ear-wearable device 100 may include more than two contact pins that are similarly disposed with respect to tunnel 108 as contact pin 202 and contact pin 204. For example, contact pin 202 and contact pin 204 may serve to provide electrical energy to recharge a battery of ear-wearable device 100 and two additional contact pins disposed within tunnel 108 may be used for communication of data between ear-wearable device 100 and another device via a cable.

Furthermore, as shown in the example of FIG. 2, ear-wearable device 100 may include a plug-stop member 228. Plug-stop member 228 may extend outwardly from tunnel wall 116 toward lengthwise axis 224 of tunnel 108 at a distance from lateral portal 110 of tunnel 108 to limit a maximum insertion depth of cable plug 200 into tunnel 108. In other words, plug-stop member 228 may stop cable plug 200 from being inserted too far into tunnel 108. If cable plug 200 were to be inserted too far into tunnel 108, terminal 218 would not be in electrical contact with contact pin 202 and/or terminal 220 would not be in electrical contact with contact pin 204.

In other examples, ear-wearable device 100 does not include a distinct plug-stop member, such as plug-stop member 228. For instance, in some such examples, plug-stop member 228 may be replaced with a bend or corner in tunnel 108. In such examples, tunnel wall 116 itself may serve to stop cable plug 200 from being inserted too far into tunnel 108.

FIG. 3 is an illustration of an example faceplate 300 manufactured in accordance with a technique of this disclosure. In some examples, such as the example of FIG. 3, shell 102 of ear-wearable device 100 (FIG. 1) may comprise faceplate 300 and a shell component that is shaped to define an interior cavity and tunnel 108. Electronic components 216 (FIG. 2) may be contained within the interior cavity. The interior cavity may be open-ended toward the user's lateral side when worn. Faceplate 300 may serve to cover the open end of the interior cavity defined by the shell component. In the example of FIG. 3, the medial surface of faceplate 300 is shown. Faceplate 300 may be shaped differently than shown in FIG. 3 to provide customization to the user's unique anatomy.

Faceplate 300 is shaped to define a protrusion 302 extending from the medial surface of faceplate 300. Protrusion 302 may be shaped to correspond to a complementary recess defined in the shell component of shell 102. An example of the recess described below with respect to FIG. 4. A segment of tunnel 108 is defined in faceplate 300. In the portion of the segment of tunnel 108 passing through protrusion 302, a section of tunnel wall 116 is not present. When faceplate 300 is assembled with shell 102, contact pins 202 and 204 and a portion of shell 102 fill in the section of tunnel wall 116 not present in protrusion 302 of faceplate 300.

Elastomeric spring pad 226 may be disposed at a location in the portion of tunnel wall 116 defined by protrusion 302 of faceplate 300. Thus, elastomeric spring pad 226 may be disposed in such a way that, when faceplate 300 is assembled with shell 102, pressure applied by elastomeric spring pad 226 to cable plug 200 (FIG. 2) when cable plug 200 is inserted into tunnel 108 forces terminal 218 of cable plug 200 into electrical contact with distal end 210 of contact pin 202 and forces terminal 220 of cable plug 200 into electrical contact with distal end 214 of contact pin 204.

Faceplate 300 is further shaped to define keying features 304. In the example of FIG. 3, keying features 304 are cuboid protrusions at the base of protrusion 302. Keying features 304 engage corresponding keying features of the shell component to help ensure correct positioning of faceplate 300.

Figure 4:
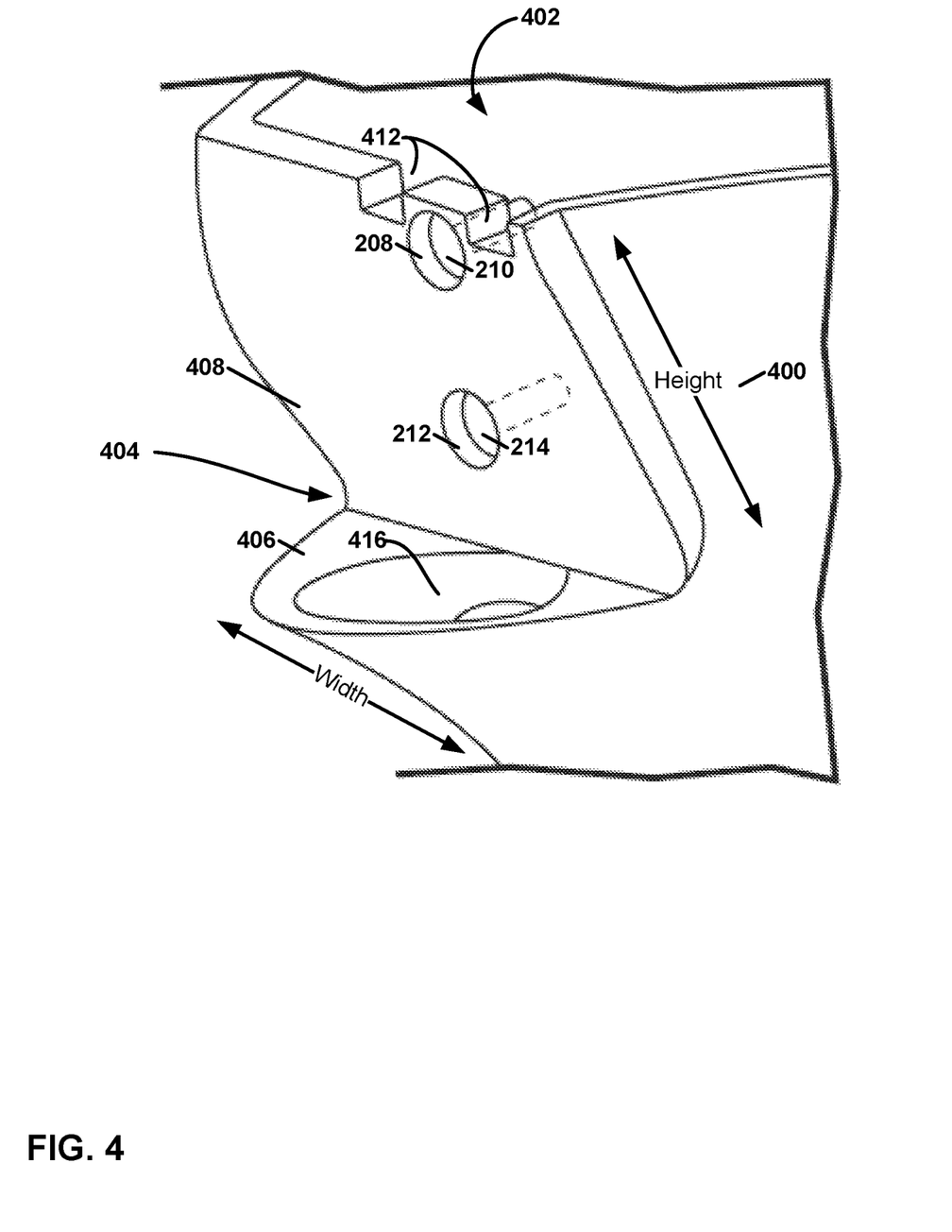
FIG. 4 is an illustration of a portion of an example of a shell component that is complementary with the faceplate of FIG. 3.

FIG. 4 is an illustration of a portion of an example of shell component 400 that is complementary with faceplate 300 of FIG. 3. Shell component 400, together with faceplate 300 and potentially one or more other shell components, may form shell 102. An interior cavity 402 of shell 102 is defined by shell component 400 and is visible in FIG. 4. Furthermore, in the example of FIG. 4, shell 102 is shaped to define a step-shaped recess 404 having a floor 406 and a riser 408. An opening 414 of a segment of tunnel 108 is defined in floor 406. A height of riser 408 may be generally equal to a height of protrusion 302 of faceplate 300. A width of riser 408 and a width of floor 406 are generally equal to corresponding widths of protrusion 302 of faceplate 300.

Contact pin aperture 208 and contact pin aperture 212 are defined in riser 408. As shown in FIG. 4, distal end 210 of contact pin 202 is visible through contact pin aperture 208. Distal end 214 of contact pin 204 is visible through contact pin aperture 212.

Furthermore, as shown in the example of FIG. 4, shell component 400 is shaped to define keying features 412. Keying features 412 of shell component 400 may engage keying features 304 of faceplate 300 when faceplate 300 is installed on shell component 400. The engagement of keying features 412 and keying features 304 may help to ensure stable positioning of faceplate 300 relative to shell 102.

Figure 5:
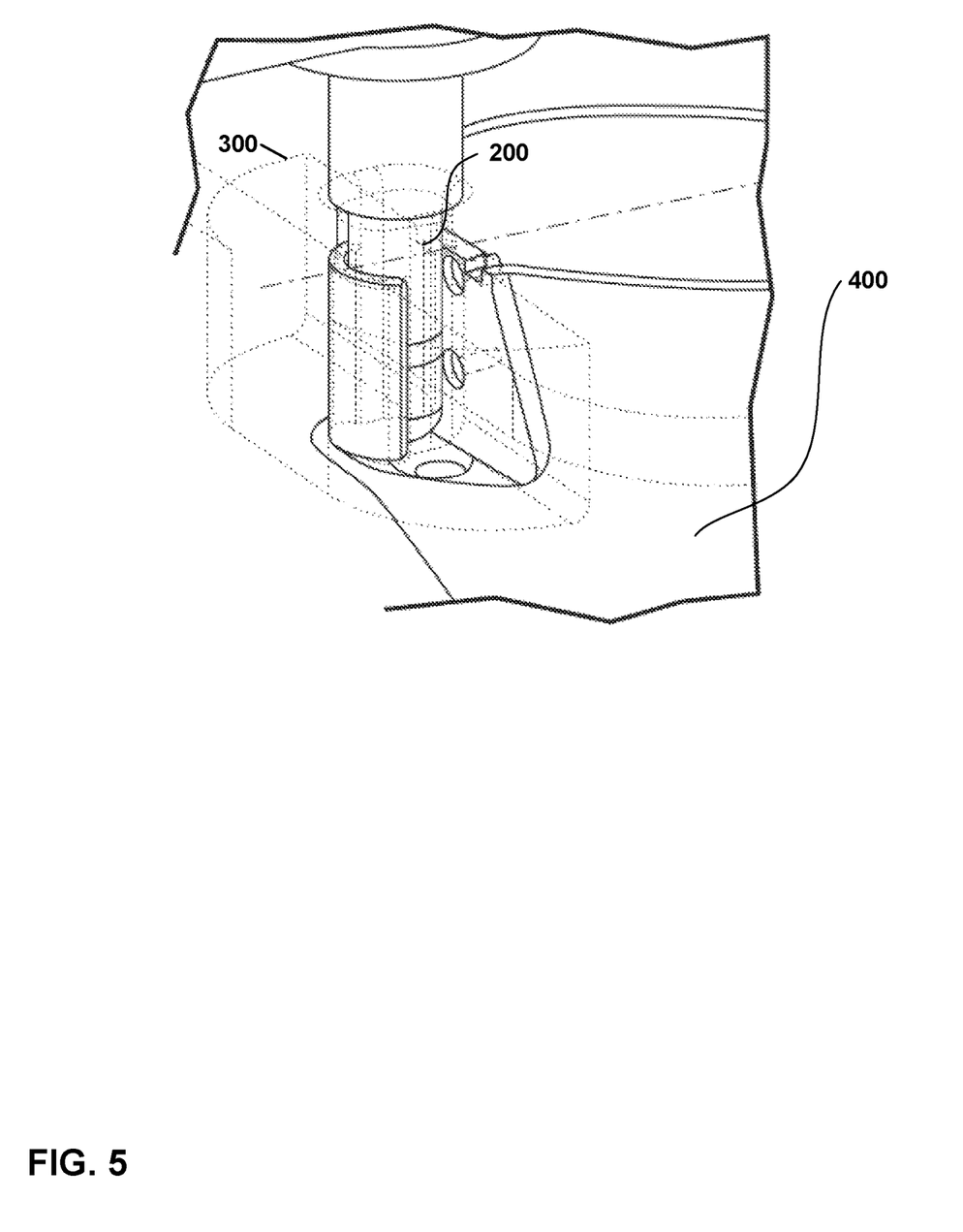
FIG. 5 is an illustration of a protrusion of the faceplate engaged with a recess of the shell component.

FIG. 5 is an illustration of protrusion 302 of faceplate 300 engaged with recess 404 of shell component 400. In the example of FIG. 5, faceplate 300 is shown in silhouette. Furthermore, FIG. 5 shows cable plug 200 inserted into tunnel 108. Thus, terminals 218 and 220 may be in electrical contact with distal end 210 of contact pin 202 and distal end 214 of contact pin 204. As shown in the example of FIG. 5, plug-stop member 228 is formed at the bottom of protrusion 302 of faceplate 300. As discussed above, plug-stop member 228 may limit the insertion depth of cable plug 200 into shell 102, reducing or eliminating the possibility of cable plug 200 breaking out through tunnel 108. Plug-stop member 228 may also help to ensure electrical contact between terminal 218 and contact pin 202 and between terminal 220 and contact pin 204. In some examples, this may allow up to a ½ millimeter variance in insertion depth to be tolerated.

Thus, in the example of FIG. 5 and other examples, shell 102 may comprise faceplate 300 and shell component 400. Shell component 400 is shaped to define interior cavity 402 containing electrical components 216. Faceplate 300 is shaped to cover an opening of interior cavity 402. Furthermore, faceplate 300 is shaped to define protrusion 302, which is shaped to engage recess 404 defined in shell component 400. Recess 404 is defined by a floor 406 of shell component 400 and a riser 408 of shell component 400. Protrusion 302 forms a sector of a segment of tunnel wall 116 and riser 408 defines a sector of the segment of tunnel wall 116 complementary to the sector of the segment of tunnel wall 116 formed by protrusion 302. Thus, the sector formed by protrusion 302 and the sector formed by riser 408 may together form a completely enclosed circle or other shape. Contact pin aperture 208 and contact pin aperture 212 are defined in the sector of the segment of tunnel wall 116 formed by riser 408.

Figure 6:
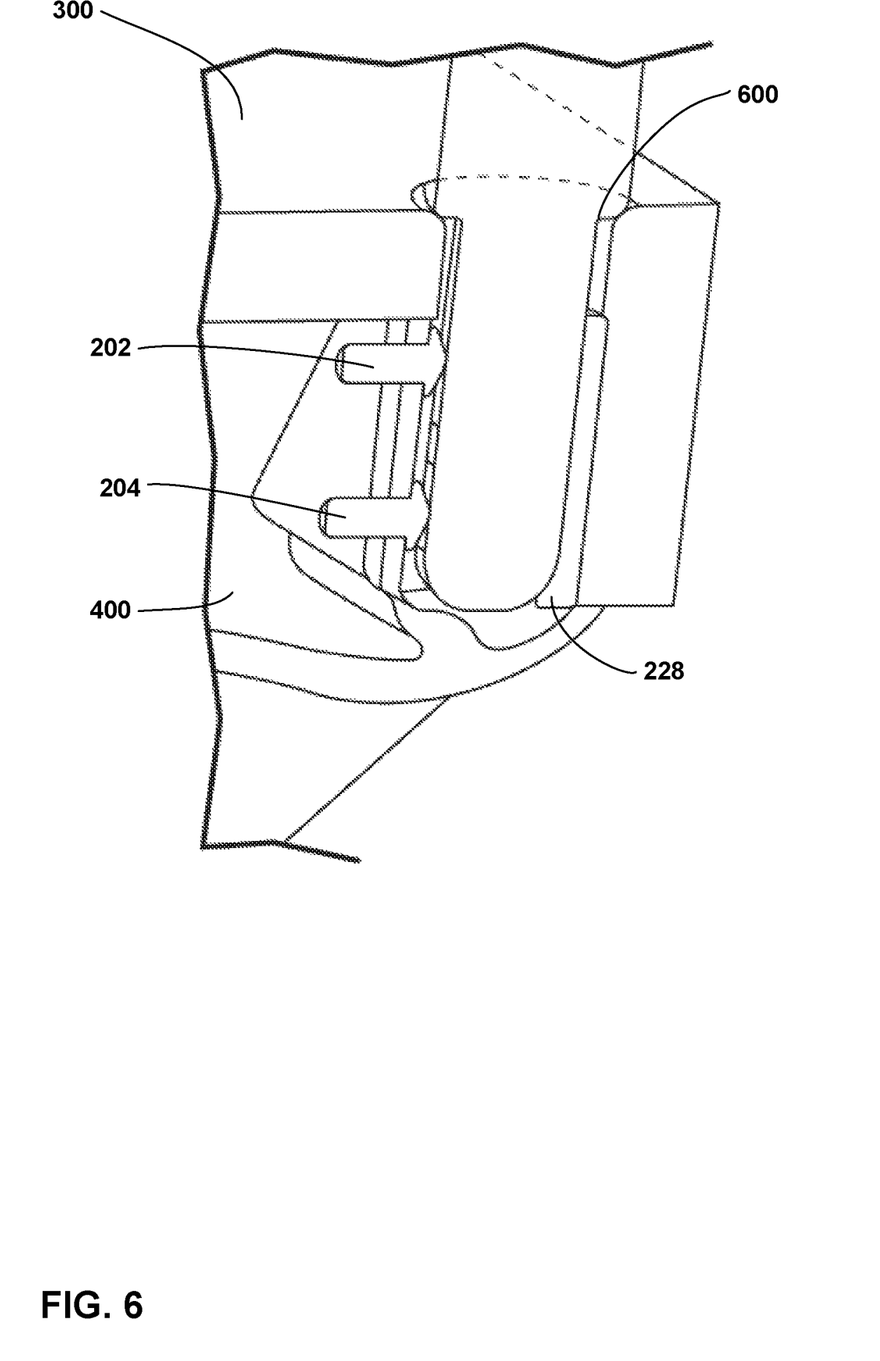
FIG. 6 is another view of the faceplate when installed on the shell component.

FIG. 6 is another view of faceplate 300 when installed on shell component 400. As shown in the example of FIG. 6, faceplate 300 may be shaped to define plug-stop member 228. Additionally, as shown in the example of FIG. 6, cable plug 200 may be shaped to define a lip 600 that may also server to prevent over-insertion of cable plug 200 into tunnel 108.

Figure 7:
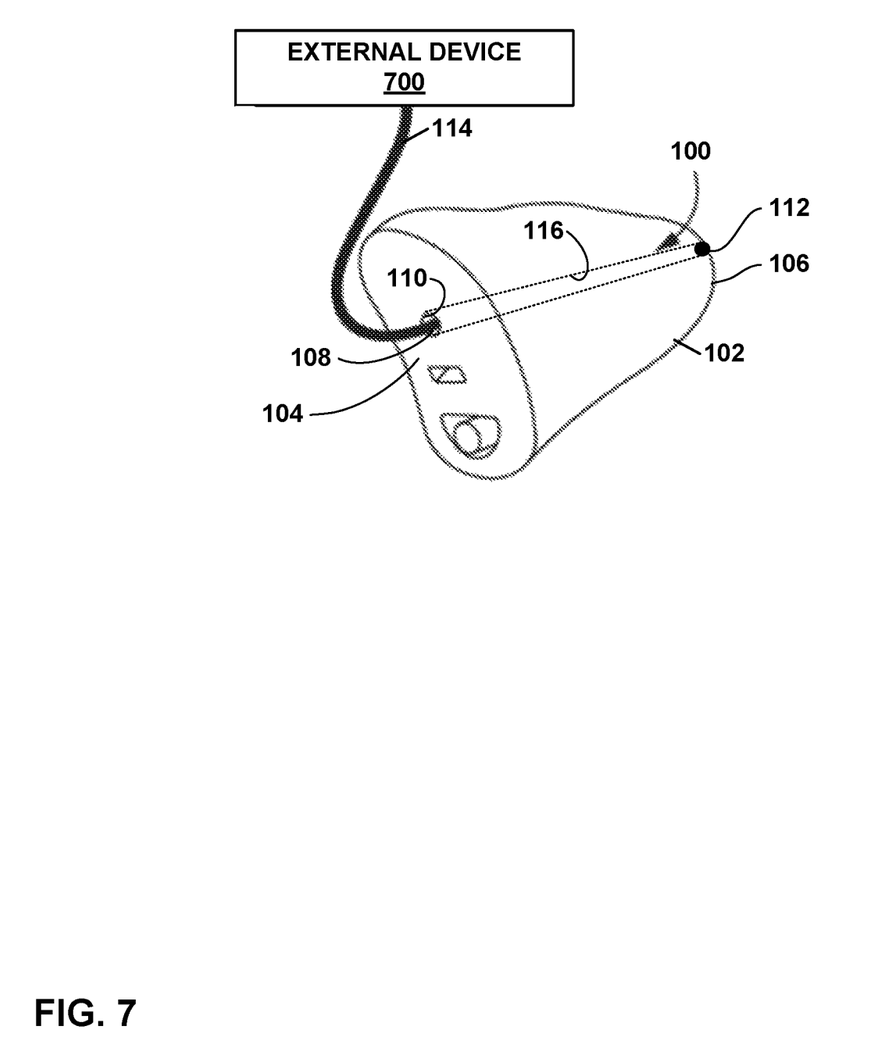
FIG. 7 illustrates an example system comprising an ear-wearable device and an external device in accordance with one or more techniques of this disclosure.

FIG. 7 illustrates an example system comprising ear-wearable device 100 and an external device 700 in accordance with one or more techniques of this disclosure. External device 700 may be a device connected to an end of cable 114 opposite the end having the cable plug (i.e., the end inserted into tunnel 108 of ear-wearable device 100. External device 700 may be one of various types of devices. For example, external device 700 may comprise a portable battery back-up device, a smartphone, a media playback device, a media streaming device, a behind-the-ear unit of a RIC hearing aid, or another type of device.

In some examples, a user may continue to use ear-wearable device 100 while the cable plug 200 is inserted into tunnel 108 and an opposite end of cable 114 is connected to external device 700. For example, ear-wearable device 100 may continue operating as a hearing aid while cable plug 200 is inserted into tunnel 108. In another example, ear-wearable device 100 may continue acting as an earphone while cable plug 200 is inserted into tunnel 108. Thus, in examples where cable 114 is used for recharging a battery of ear-wearable device 100, the user may continue using ear-wearable device 100 while the battery of ear-wearable device 100 is being recharged. This may be an especially useful function when the other end of cable 114 is attached to a portable recharging battery pack. In examples where ear-wearable device 100 acts as an earphone, ear-wearable device 100 may typically receive streams of media data via a wireless antenna. However, when the battery level of a rechargeable battery of ear-wearable device 100 is low or there is excessive radio interference, cable 114 may be used to provide either or both energy for both recharging the battery and media data to ear-wearable device 100. For instance, in such an example, ear-wearable device 100 may act like a conventional wired earphone. In such examples, external device 700 may be a smartphone, tablet computer, portable gaming device, or another type of media device.

In some examples, external device 700 comprises a sensor unit. The sensor unit may comprise a device separate from ear-wearable device 100. The sensor unit may include one or more sensors, such as sensors for detecting biological information regarding the user of ear-wearable device 100. For instance, the sensors may include a heart rate sensor, a blood pressure sensor, a transdermal blood oxygenation sensor, or another type of sensor. In some examples, the sensor unit may be configured to rest in or proximate to the user's ear. For instance, the sensor unit may rest in the concha, tragus, scapha, or other part of the user's ear. The sensor unit may use cable 114 to communicate data to ear-wearable device 100. Ear-wearable device 100 may store the data from the sensor unit in a memory. In some examples, ear-wearable device 100 may send data from the sensor unit to another device (e.g., a smartphone, personal computer, etc.) wirelessly or via another cable insertable into tunnel 108. In some examples, one or more processors in ear-wearable device 100 may process the sensor data and output audible sound based on the sensor data. For instance, ear-wearable device 100 may alert the user to slow their heart rate.

Figure 8:
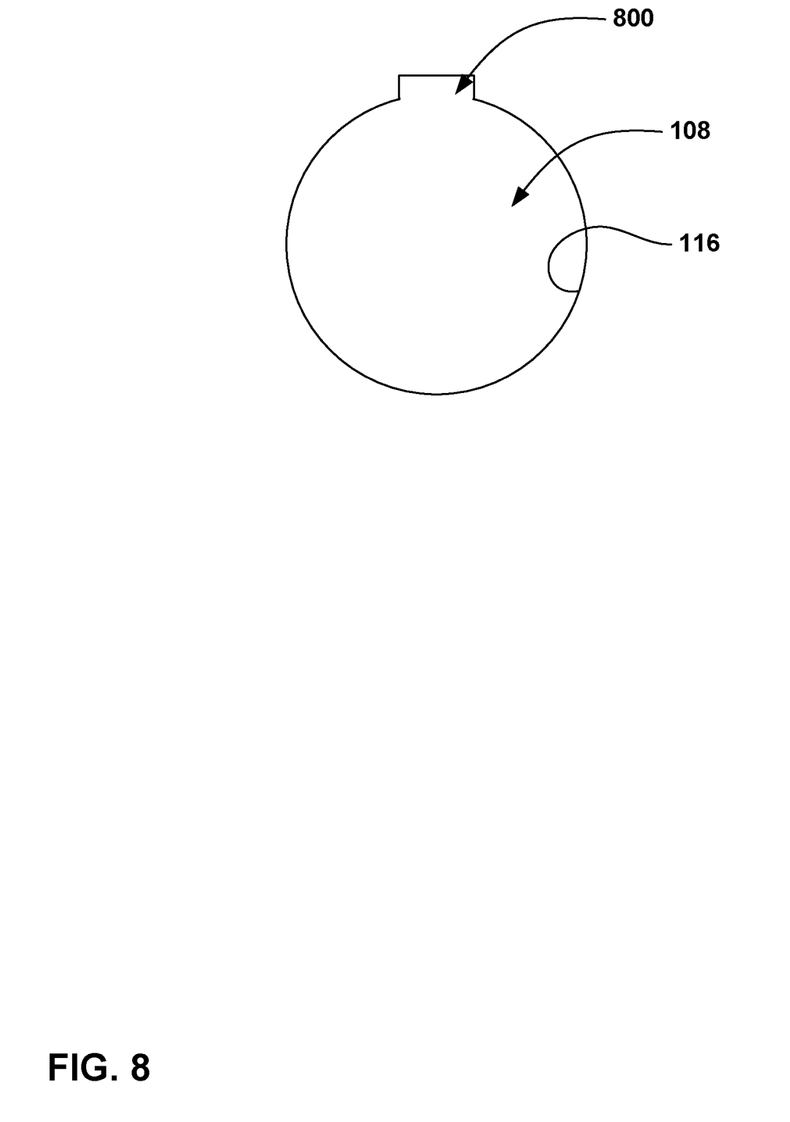
FIG. 8 is a conceptual diagram illustrating an example cross section of tunnel 108, in accordance with a technique of this disclosure.

FIG. 8 is a conceptual diagram illustrating an example cross section of tunnel 108, in accordance with a technique of this disclosure. As described elsewhere in this disclosure, in some examples, ear-wearable device 100 may continue to be used while cable plug 200 is inserted into tunnel 108. As shown in the example of FIG. 8, tunnel wall 116 may be shaped to define a trench 800. Trench 800 may run from lateral portal 110 of tunnel 108 at least through a maximum insertion depth of cable plug 200. Trench 800 may allow internally-generated sound to continue to escape while cable plug 200 is inserted into tunnel 108. In other examples, the need for trench 800 may be obviated by shell 102 being shaped to have a trench vent running along an outer surface of ear-wearable device 100.

Various examples have been described. These and other examples are within the scope of the following claims.

What is claimed is:

1. An ear-wearable device comprising:
   a shell shaped for wearing in an ear of a user, wherein:
     the shell comprises a tunnel wall,
       the tunnel wall being a portion of the shell shaped to define a tunnel that is open-ended and passes through the ear-wearable device;
   two or more contact pins positioned within the shell;
   the tunnel wall being shaped such that the tunnel wall defines one or more contact pin apertures through which distal ends of the contact pins pass;
   one or more electrical components encased within the shell, the contact pins being conductors from the one or more electrical components, wherein:
     the shell comprises a faceplate and a shell component,
     the shell component is shaped to define an interior cavity containing the one or more electrical components,
     the faceplate is shaped to cover an opening of the interior cavity,
     the faceplate is shaped to define a protrusion shaped to engage a recess defined in the shell component,
     the recess is defined by a floor portion of the shell component and a riser portion of the shell component,
     the protrusion forms a sector of a segment of the tunnel wall and the riser portion of the shell component defines a sector of the segment of the tunnel wall complementary to the sector of the segment of the tunnel wall formed by the protrusion, and
     the first contact pin aperture and the second contact pin aperture are defined in the sector of the segment of the tunnel wall formed by the riser portion of the shell component; and
   wherein the distal ends of the contact pins are positioned to make electrical contact with terminals of a cable plug that is removably inserted into the tunnel.

2. The ear-wearable device of claim 1, further comprising:
   an elastomeric spring pad disposed on the shell, wherein pressure applied by the elastomeric spring pad to the cable plug inserted into the tunnel forces the terminals of the cable plug into electrical contact with the distal ends of the contact pins.

3. The ear-wearable device of claim 1, further comprising a plug-stop member extending outwardly from the tunnel wall toward a lengthwise axis of the tunnel at a distance from a lateral portal of the tunnel, wherein the plug-stop member limits a maximum insertion depth of the cable plug into the tunnel.

4. The ear-wearable device of claim 1, wherein the contact pins are mounted within the shell such that the contact pins are immovable relative to the shell.

5. The ear-wearable device of claim 1, wherein:
the tunnel is a vent, and
the shell is shaped such that during wear of the ear-wearable device, a medial portal of the tunnel is located inside an ear canal of the ear of the user.

6. The ear-wearable device of claim 1, wherein the shell is shaped such that during wear of the ear-wearable device, a medial portal of the tunnel is located in a concha of the ear of the user.

7. The ear-wearable device of claim 1, wherein the one or more electrical components comprise a battery configured to be recharged using electrical energy supplied through the cable plug and two or more of the contact pins.

8. The ear-wearable device of claim 1, wherein the one or more electrical components are configured to process data transmitted to the ear-wearable device through the cable plug and two or more of the contact pins.

9. The ear-wearable device of claim 1,
wherein the one or more electrical components comprise a battery configured to be recharged using electrical energy supplied through the cable plug and a first set of two or more of the contact pins, and
wherein the one or more electrical components are configured to process data transmitted to the ear-wearable device through the cable plug and a second set of two or more of the contact pins.

10. The ear-wearable device of claim 1, wherein the tunnel wall is shaped to form a trench running from a lateral portal of the tunnel at least through a maximum insertion depth of the cable plug.

11. The ear-wearable device of claim 1, wherein the ear-wearable device is configured to continue operating as a hearing aid while the cable plug is inserted in the tunnel.

12. The ear-wearable device of claim 1, wherein:
the shell has a lateral surface and a medial surface,
the lateral surface of the shell is distal to a midline of the user when the ear-wearable device is worn by the user, the medial surface of the shell is proximal to the midline of the user when the ear-wearable device is worn by the user, and
the tunnel passes through the ear-wearable device from the lateral surface of the shell to the medial surface of the shell and is open at both the lateral surface of the shell and the medial surface of the shell.

13. A system comprising:
a cable having a cable plug;
an ear-wearable device comprising:
a shell shaped for wearing in an ear of a user, wherein the shell comprises a tunnel wall, the tunnel wall being a portion of the shell shaped to define a tunnel that is open-ended and passes through the ear-wearable device;
two or more contact pins positioned within the shell;
the tunnel wall being shaped such that the tunnel wall defines one or more contact pin apertures through which distal ends of the contact pins pass; and
one or more electrical components encased within the shell, the contact pins being conductors from the one or more electrical components,
wherein the distal ends of the contact pins are positioned to make electrical contact with terminals of the cable plug that is removably inserted into the tunnel; and
a sensor unit connected to an end of the cable opposite an end of the cable having the cable plug, the sensor unit including one or more sensors, and the sensor unit configured to rest in or proximate the ear of the user.

14. The system of claim 13, wherein the ear-wearable device further comprises an elastomeric spring pad disposed on the shell, wherein pressure applied by the elastomeric spring pad to the cable plug inserted into the tunnel forces the terminals of the cable plug into electrical contact with the distal ends of the contact pins.

15. The system of claim 13, wherein the ear-wearable device further comprises a plug-stop member extending outwardly from the tunnel wall toward a lengthwise axis of the tunnel at a distance from a lateral portal of the tunnel, wherein the plug-stop member limits a maximum insertion depth of the cable plug into the tunnel.

16. The system of claim 13, wherein the contact pins are mounted within the shell such that the contact pins are immovable relative to the shell.

17. The system of claim 13, wherein:
the tunnel is a vent, and
the shell is shaped such that during wear of the ear-wearable device, a medial portal of the tunnel is located inside an ear canal of the ear of the user.

\* \* \* \* \*